US006222071B1

(12) United States Patent
Delalu et al.

(10) Patent No.: US 6,222,071 B1
(45) Date of Patent: Apr. 24, 2001

(54) SYNTHESIS METHOD FOR SOLUTION WITH HIGH GRADE CHLORAMINE

(75) Inventors: Henri Delalu, Lyons; Laurent Peyrot, Meyzieu; Mazen Elkhatib, Villeurbanne; Jean-Jacques Counioux, Lyons; Armand Cohen, Bolbec, all of (FR)

(73) Assignee: Adir et Compagine, Courbevoie (FR)

( * ) Notice: Subject to any disclaimer, the term of this patent is extended or adjusted under 35 U.S.C. 154(b) by 0 days.

(21) Appl. No.: 09/509,644

(22) PCT Filed: Sep. 29, 1998

(86) PCT No.: PCT/FR98/02081

§ 371 Date: Mar. 29, 2000

§ 102(e) Date: Mar. 29, 2000

(87) PCT Pub. No.: WO99/16707

PCT Pub. Date: Apr. 8, 1999

(30) Foreign Application Priority Data

Sep. 30, 1997 (FR) .................................................. 97 12109

(51) Int. Cl.⁷ .................................................. C07C 239/04
(52) U.S. Cl. .............................................................. 564/118
(58) Field of Search ................................................ 564/118

(56) References Cited

U.S. PATENT DOCUMENTS 3,254,952   6/1966   Raleigh et al. .
5,273,678 * 12/1993   Deroux et al. .................. 252/187.26

FOREIGN PATENT DOCUMENTS

| 0277267 A1 | * | 8/1988  | (EP) | ............................. C07D/209/52 |
| 0462016 A1 | * | 12/1991 | (EP) | ............................. C07D/209/08 |
| 2 610 321  |   | 8/1988  | (FR) . |   |
| 2 663 324  |   | 12/1991 | (FR) . |   |

* cited by examiner

Primary Examiner—Johann Richter
Assistant Examiner—Brian J. Davis
(74) Attorney, Agent, or Firm—The Firm of Hueschen and Sage; G. Patrick Sage

(57) ABSTRACT

The present invention relates to a process for the preparation of high-grade chloramine by the action of commercial eau de Javelle of 100 chlorometric degrees on a solution of ammonia in the presence of ammonium chloride. According to this process, the chloramine is obtained having a content greater than or equal to 2 mol $L^{-1}$, that is to say, greater than or equal to 10.3%. The process can be carried out continuously or discontinuously.

12 Claims, No Drawings

SYNTHESIS METHOD FOR SOLUTION WITH HIGH GRADE CHLORAMINE

The present application is a U.S. National Application filed under 35 USC 371 of PCT/FR98/02081, filed Sep. 29, 1998 based upon French application Serial No. 97.12109 filed Sep. 30, 1997.

The present invention relates to a process for the preparation of high-grade chloramine by the action of commercial eau de Javelle of 100 chlorometric degrees on a solution of ammonia in the presence of ammonium chloride. According to this process, the chloramine is obtained having a content greater than or equal to 2 mol $L^{-1}$, that is to say greater than or equal to 10.3%. The process can be carried out continuously or discontinuously. Besides its applications as a bleaching, disinfecting and bactericidal agent, monochloramine is used in numerous reactions as a synthesis intermediate. In particular, it is the principal reagent in the synthesis of pharmaceutically valuable hydrazines by the Raschig process. For example, N-amino-2-methylindoline and N-amino-3-azabicyclo[3.3.0]octane are prepared by reacting $NH_2Cl$ with 2-methylindoline and 3-azabicyclo[3.3.0]octane according to the processes described in patent Specifications EP 462 016 and EP 277 267.

That method of preparation is currently attracting a great deal of interest in view of the fact that it causes little pollution compared with the prior methods of preparation, which make use of N-nitroso compounds. It does, however, have disadvantages associated with the low hydrazine content of the reaction liquors, which generally does not exceed 2 to 4%. That limitation is linked principally to the fact that the reagents, and especially sodium hypochlorite, are highly diluted, necessitating complicated and onerous extraction procedures. As a result, the momentary concentration of chloramine in the reactor does not, even in the best of cases, exceed 1 mol $L^{-1}$ (5.15%).

In view of the fact that $NH_2Cl$ is highly unstable in aqueous solution, synthesis in a more concentrated medium has not been attempted. Its instability is linked to competition between hydrolysis and autocatalytic dismutation reactions, which result in rapid acidification of the medium and in the preponderant formation of dichloramine and nitrogen chloride. In a non-buffered medium the degradation can rapidly result in the solution boiling. Obtaining a higher monochloramine titre requires the use of a new reagent of a high chlorometric degree and research into appropriate operating conditions.

The present invention makes it possible to double, at least, the $NH_2Cl$ titre by using solutions of eau de Javelle of the order of 100 chlorometric degrees and employing conditions compatible with obtaining high-grade (H.G.) chloramine. This new process makes it possible, starting from an identical unit volume of hypochlorite, to double the productivity in terms of hydrazine and to make savings in raw materials and energy in the synthesis, reagent recycling and distillation procedures.

Because oxidation of ammonia by sodium hypochlorite is an exothermic reaction, it must be carried out at low temperature in order to limit the degradation reactions. It is therefore necessary to cool the reagents beforehand, prior to their injection. For example, for a solution of eau de Javelle of 48 chlorometric degrees (crystallisation point=–21.4° C.), the temperature inside the reactor must not be higher than –5° C. That limit has to be lower for an NaOCl content that is twice as high. Unlike hypochlorite at 2.14 mol $L^{-1}$ (48° chl.), a solution of eau de Javelle of 100 chlorometric degrees crystallises in a stirred medium at 14° C. Crystallisation nevertheless remains difficult unless initiated. In a still medium, therefore, a very clear delay in crystallisation is observed and it is thus possible to maintain H.G. eau de Javelle solutions in a single-phase medium for several hours at –20° C. in glass vessels. However, in spite of the solution having little tendency to crystallise, it is necessary in the case of continuous industrial synthesis to use the H.G. eau de Javelle at approximately 14° C. in order to avoid possible caking in the pipework.

As in the process for the preparation of $NH_2Cl$ starting from sodium hypochlorite of 48 chlorometric degrees, it is necessary to introduce into the ammonia-containing reagent an amount of an acceptor compound that is able to neutralise completely the hydroxyl ions formed in situ by the reaction:

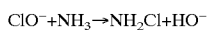
$ClO^- + NH_3 \rightarrow NH_2Cl + HO^-$

The acceptor may be an acid, a water-soluble acid salt or a water-soluble neutral salt. It is, however, preferable to use an ammonium salt of the type $(NH_4^+)H^+_\beta A^{(1+\beta)-}$ wherein $\beta$ is 0 or 1 and A is Cl, $CO_3$ or $NO_3$ so as to buffer the reaction medium at approximately the pKa of $NH^+_4/NH_3$, to eliminate the $HO^-$ ions and to keep the concentration of free ammonia constant:

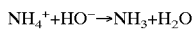
$NH_4^+ + HO^- \rightarrow NH_3 + H_2O$

Furthermore, the combined ammoniacal mixture must be cooled to well below –10° C. so as to absorb the heat given off and to compensate for the heating associated with the injection of the hypochlorite at a temperature above its crystallisation temperature. Under those conditions, the cooling effect introduced principally by the ammoniacal solution avoids the use of eau de Javelle in a supercooled state and hence ensures synthesis in a homogeneous medium.

Those constraints require that new ammoniacal combinations having a low crystallisation point of from –20° C. to –30° C. be found. The composition of those mixtures is determined by the content of the hypochlorite solutions. The latter have a titre of about 100 chlorometric degrees, which means that, under normal conditions, one liter releases 100 liters of chlorine under the action of hydrogen chloride. The molar concentration of NaOCl is then 4.46 mol $L^{-1}$. Unlike the extracts of 48 chlorometric degrees, the NaCl and NaOCl titres are not in equimolecular proportions.

To obtain quantitative yields, the conditions of synthesis must meet the following criteria:

The H.G. eau de Javelle can be used in the supercooled state but, in order to prevent any initiation of crystallisation, it is preferable to inject it at a temperature higher than or equal to 15° C. The H.G. eau de Javelle is relatively stable and loses, per 24 hours, approximately 1.3 degrees at 17° C. or 0.47 degree at 10° C.

The overall content of Lewis acid must be sufficient to neutralise at least 90% of the hydroxyl ions resulting from the $NH_3$/NaOCl reaction.

The pH must be maintained at from 10 to 12, preferably at approximately 10.5.

The ratio [total ammonia]/[$ClO^-$] must be from 2 to 5 (preferably 2.7) so as to stabilise the chloramine that is formed.

The crystallisation point of the $(NH_4^+)H^+_\beta A^{(1+\beta)-}/NH_3/H_2O$ wherein $\beta$ is 0 or 1 and A is Cl, $CO_3$ or $NO_3$ ternary mixture must be from –20 to –30° C. so as to offset the frigorific deficit associated with the injection of the chlorinated reagent at T≧15° C. in the context of synthesis in a single-phase medium.

The temperature inside the reactor must be in the range from −5 to −20° C., preferably about −15° C.

A large number of acids (HCl, $H_2SO_4$, etc.), neutral salts ($CaCl_2$, $MgCl_2$, $ZnSO_4$, etc.) and acid salts ($NaH_2PO_4$, $NH_4HCO_3$, $NH_4Cl$, $NH_4NO_3$, etc.) may be used in the synthesis of chloramine. A priori, certain of those are extremely interesting because they possess more than one acid functionality in the same molecule. On the other hand, very few are soluble and precipitate below 0° C. At this stage, the ammonium salts are the most advantageous since they exhibit greater solubility, which increases as the ammonia content of the medium increases.

Under the conditions of synthesis defined above, use of polythermal diagrams involving the $NH^+_4$ ion shows that the ammoniacal combinations meeting the above criteria require the use of ammonium nitrate : $NH_3$—$NH_4Cl$—$NH_4NO_3$—$H_2O$ or $NH_3$—$NH_4NO_3$—$H_2O$. Those combination mixtures allow operation in a homogeneous medium down to a temperature of −30° C. In the absence of $NH_4NO_3$, the preparation of the H.G. chloramine can be carried out only in batches. In fact, at the start of the reaction, a fraction of the neutralisation salt is insoluble; the mixture then becomes rapidly homogeneous as a result of dilution and neutralisation of the $HO^-$ ions.

Thus, according to the invention, the continuous preparation of chloramine in a homogeneous medium must be carried out in the presence of an ammoniacal combination based on ammonium nitrate $(NH_3/(NH^+_4)_\alpha H^+_\beta A^{(\alpha+\beta)-}/NH_4NO_3/H_2O)$, wherein α is 0 or 1, β is 0 or 1, and A is Cl or $CO_3$ preferably $NH_3/NH_4NO_3/H_2O$ or $NH_3/NH_4Cl/NH_4NO_3/H_2O$; the discontinuous preparation of chloramine must be carried out using mixtures of the type $NH_3/(NH_4^+)H^+_\beta A^{(1+\beta)-}/H_2O$ wherein β is 0 or 1 and A is Cl, $CO_3$ or $NO_3$, preferably $NH_3/NH_4Cl/H_2O$, which may be partially insoluble in the course of the addition of the chlorinated reagent.

The following Examples illustrate the process of the invention carried out discontinuously and continuously, without limiting it:

EXAMPLE I

The reaction is carried out in a cylindrical, double-wall reactor made from borosilicate glass maintained at −20° C. by circulation of a thermostatic fluid. The ammoniacal solution has a titre of 7.2 mol $L^{-1}$ for $NH_3$ and 4.76 mol $L^{-1}$ for $NH_4Cl$, which corresponds to the following composition by weight: 12.1% $NH_3$, 25.2% $NH_4Cl$, 62.7% $H_2O$. 30 ml of that mixture are then introduced into the vessel with stirring until thermal equilibrium is reached. The sodium hypochlorite solution (104.4 chlorometric degrees; 4.64 mol $L^{-1}$), in the supercooled state, is then poured in at a regular rate (duration of addition 10 minutes) in such a manner that the temperature inside the reactor does not exceed −10° C. Since the point representing the ammoniacal mixture is located, at the start of the reaction, within the liquid+$NH_4Cl$ two-phase region of the diagram for the ternary composition $NH_3$—$NH_4Cl$—$H_2O$ (isotherm −20° C.), 29.3% of the initial amount of ammonium chloride are precipitated. In the course of the addition of NaOCl, the mixture rapidly becomes homogeneous as a result of dilution and elimination of the hydroxyl ions. At the end of the reaction a chloramine solution is obtained having a titre of 2.18 mol $L^{-1}$ (11.2%), which corresponds to a yield of 98% relative to the hypochlorite. Under the conditions described in this experiment, the high-grade $NH_2Cl$ solution formed is relatively stable at −20° C. and loses only 1.4% after 15 minutes.

EXAMPLE II

Carrying out the synthesis under the same conditions but without initial precipitation of $NH_4Cl$ (homogeneous medium) requires the ammonium chloride content to be reduced. As the saturation curve for the ternary mixture shows, the $NH_3$ titre has to be increased (injection of gaseous $NH_3$) so as to dissolve $NH_4Cl$. Starting, for example, from a commercial 32% ammonia solution, the maximum dissolved amount of $NH_4Cl$ allowed by the −20° C. isotherm corresponds to the following overall composition: 25.3% $NH_3$ (14.25 mol $L^{-1}$), 20.9% $NH_4Cl$ (3.74 mol $L^{-1}$). A concentrated $NH_2Cl$ solution is obtained having a titre of 1.99 mol $L^{-1}$ (10.2%), that is to say a yield of 90% relative to NaOCl. That slight decrease in the yield is due to 16% of the reaction having been carried out in a non-buffered medium.

EXAMPLE III

This test was carried out using a hypochlorite solution no longer in the supercooled state but at a temperature above its crystallisation point (+15° C.). 30 ml of a combined ammoniacal solution having titres of 12.4 mol $L^{-1}$ for $NH_3$ (21.2%) and 5 mol $L^{-1}$ for $NH_4Cl$ (26.8%) are introduced into a vessel maintained at −25° C. An equivalent volume of eau de Javelle (103.8 chlorometric degrees; 4.63 mol $L^{-1}$) is then poured in dropwise (duration of addition 15 minutes) in such a manner that the temperature inside the reactor does not exceed −15° C. As in Example 1, the reaction medium is heterogeneous at first (partial precipitation of $NH_4Cl$) and results in an $NH_2Cl$ concentration of 2.19 mol $L^{-1}$ (11.3%), that is to say a yield of 94%.

EXAMPLE IV

For carrying out the preparation in a single-phase medium using eau de Javelle at +15° C. while neutralising all the $HO^-$ ions, a quaternary mixture, $NH_4Cl$—$NH_4NO_3$—$NH_3$—$H_2O$, was used. The composition thereof in terms of $NH_3$, $NH_4Cl$, $NH_4NO_3$ and $H_2O$ is 13.14 mol $L^{-1}$ (22.4%), 3.02 mol $L^{-1}$ (16.2%), 1.76 mol $L^{-1}$ (14.1%) and 26.2 mol $L^{-1}$ (47.3%), respectively. The experimental conditions are identical to Example 3. Using eau de Javelle of 98.4 chlorometric degrees (4.39 mol $L^{-1}$), an $NH_2Cl$ solution is obtained having a titre of 2.01 mol $L^{-1}$ (yield 90%), that is to say a content in terms of weight of 10.3%.

EXAMPLE V

This test is identical to Example 4, but with all the ammonium chloride being replaced by ammonium nitrate. Thus, starting from eau de Javelle of 4.65 mol $L^{-1}$ (104.3 chlorometric degrees) and an ammoniacal mixture of 7.55 mol $L^{-1}$ of $NH_3$ (12.9%) and 5 mol $L^{-1}$ of $NH_4Cl$ (27%), the yield of the reaction establishes itself at 95%, which corresponds to an $NH_2Cl$ solution of 2.21 mol $L^{-1}$ (11.4%).

EXAMPLE VI

Continuous synthesis of H.G. chloramine

The chloramine synthesis is carried out in a stirred cylindrical continuous reactor maintained at a temperature of from −20 to −30° C. Two lateral inlets in diametrically opposite positions allow the H.G. hypochlorite and ammoniacal solutions to be introduced continuously. The co-reagents are cooled beforehand by circulation in two spiral coils integrated in two cylindrical thermostatic jackets. Their composition corresponds to that defined in Example 4. The flow rates in terms of mass are pre-regulated so that the injection is equivolumetric (4 ml.min$^{-1}$). The injection temperatures for the reagents were fixed at 15 and −30° C. for NaOCl and the quaternary mixture NH$_4$Cl—NH$_4$NO$_3$—NH$_3$—H$_2$O, respectively. The temperature prevailing within the reaction mixture is −11° C. At the reactor outlet, an NH$_2$Cl solution having a titre of 2.07 mol L$^{-1}$ (10.6%) is obtained continuously.

Synthesis of N-amino-3-azabicyclo[3.3.0]octane starting from H.G. chloramine

The solutions of hydrazine (N-amino-3-azabicyclo[3.3.0]octane) were prepared by the action of 30 ml of NH$_2$Cl cooled to −15° C. on 130 g of a heteroazeotropic alkaline solution (30% 3-azabicyclo[3.3.0]octane) containing 3.8 g of sodium hydroxide. The chloramine solutions having titres of 2.18 and 2.21 mol L$^{-1}$ were synthesised according to the methods described in Examples 4 and 5, respectively. The duration of the addition is 20 minutes and the temperature of the reaction mixture is maintained at 60° C. Under those conditions, N-amino-3-azabicyclo[3.3.0]octane solutions having titres of 0.36 and 0.365 mol L$^{-1}$ (4.34 and 4.42%) are obtained, that is to say a yield of from 92 to 93% relative to NH$_2$Cl.

Synthesis of N-amino-2-methylindoline starting from H.G. chloramine

In the same manner, by proceeding under the conditions in patent Specification EP 462 016, a solution of N-amino-2-methylindoline is obtained by the action of chloramine on an alcoholic solution of 2-methylindoline.

What is claimed is:

1. Process for the synthesis of high-grade chloramine solution, wherein a sodium hypochlorite solution of approximately 100 chlorometric degrees is reacted with a combined mixture of ammonia and ammonium salts at a temperature of −5 to −20° C.

2. Process according to claim 1, wherein continuous preparation in a homogeneous medium is carried out with an ammoniacal combination based on ammonium nitrate (NH$_3$/(NH$^+_4$)$_\alpha$H$^+_\beta$A$^{(\alpha+\beta)-}$/NH$_4$NO$_3$/H$_2$O), wherein α is 0 or 1, β is 0 or 1, and A is Cl or CO$_3$.

3. Process according to claim 1, wherein discontinuous preparation is carried out using a mixture of the type NH$_3$/(NH$_4^+$)H$^+_\beta$A$^{(1+\beta)-}$/H$_2$O wherein β is 0 or 1 and A is Cl, CO$_3$ or NO$_3$.

4. Process according to claim 2; wherein the sodium hypochlorite of 100 chlorometric degrees is at a temperature higher than or equal to 15° C.

5. Process according to claim 1, wherein the ammoniacal reagent is precooled to a temperature of −20 to −30° C.

6. Process according to claim 1, wherein at least 90% of the hydroxyl ions produced by the reaction are neutralised and the pH is maintained at 10 to 12.

7. Process according to claim 1, wherein the ratio of the reagents ([NH$_3$]+[NH$^+_4$])/[ClO$^-$] is from 2 to 5.

8. Process according to claim 1, wherein continuous preparation in a homogeneous medium is carried out with an ammoniacal combination based on NH$_3$/NH$_4$NO$_3$/H$_2$O or NH$_3$/NH$_4$Cl/NH$_4$NO$_3$/H$_2$O.

9. Process according to claim 1, wherein discontinuous preparation is carried out using a mixture of the type NH$_3$/NH$_4$Cl/H$_2$O.

10. Process according to claim 3, wherein the sodium hypochlorite of 100 chlorometric degrees is at a temperature higher than or equal to 15° C.

11. Process according to claim 1, wherein at least 90% of the hydroxyl ions produced by the reaction are neutralised and the pH is maintained at approximately 10.5.

12. Process according to claim 1, wherein the ratio of the reagents ([NH$_3$]+[NH$^+_4$])/[ClO] is about 2.7.

* * * * *

UNITED STATES PATENT AND TRADEMARK OFFICE
CERTIFICATE OF CORRECTION

PATENT NO. : 6,222,071 B1
DATED : April 24, 2001
INVENTOR(S) : Henri Delalu, Laurent Peyrot, Mazen Elkhatib, Jean-Jacques Counioux, Armand Cohen It is certified that error appears in the above-identified patent and that said Letters Patent is hereby corrected as shown below:

<u>Title page, column 1,</u>
Line 5, (Starting with the word Inventors) "Lyons" should read -- Lyon --
Line 8, "Lyons" should read -- Lyon --

Signed and Sealed this

Thirteenth Day of November, 2001

Attest:

NICHOLAS P. GODICI
Attesting Officer
Acting Director of the United States Patent and Trademark Office